US 6,268,181 B1

(12) United States Patent
Manker et al.

(10) Patent No.: US 6,268,181 B1
(45) Date of Patent: *Jul. 31, 2001

(54) METHODS FOR PRODUCING A POTENTIATOR OF BACILLUS PESTICIDAL ACTIVITY

(75) Inventors: Denise Carol Manker, Davis; William D. Lidster, Sacramento; Susan C. MacIntosh, Woodland; Robert L. Starnes, Sacramento, all of CA (US)

(73) Assignee: Valent BioSciences, Corporation, Libertyville, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/015,647

(22) Filed: Jan. 28, 1998

Related U.S. Application Data

(63) Continuation of application No. 08/470,289, filed on Jun. 6, 1995, now abandoned, which is a continuation-in-part of application No. 08/295,323, filed on Aug. 23, 1994, now abandoned, which is a continuation-in-part of application No. 08/146,852, filed on Nov. 3, 1993, now abandoned, which is a continuation-in-part of application No. 08/095,240, filed on Jul. 20, 1993, now abandoned, which is a continuation-in-part of application No. 07/990,202, filed on Dec. 14, 1992, now abandoned, which is a continuation-in-part of application No. 07/971,786, filed on Nov. 5, 1992, now abandoned.

(51) Int. Cl.[7] .................................................. C12P 21/04
(52) U.S. Cl. ................... 435/71.2; 435/71.3; 435/252.5; 424/93.461; 504/117
(58) Field of Search ....................... 424/93.461; 435/71.2, 435/252.5, 69.1, 171.3, 832; 504/117

(56) References Cited

U.S. PATENT DOCUMENTS

| 3,911,110 | 10/1975 | Smirnoff . |
| 4,206,281 | 6/1980 | Goldberg . |
| 4,764,372 | 8/1988 | Herrnstadt et al. . |
| 4,766,203 | 8/1988 | Krieg et al. . |
| 5,618,692 | 4/1997 | Handelsman et al. ............... 435/69.1 |
| 5,702,703 | 12/1997 | Schnepf et al. .................. 424/93.461 |
| 5,852,054 | * 12/1998 | Handelsman ....................... 435/252.5 |

FOREIGN PATENT DOCUMENTS

| 0304178 | 2/1989 | (EP) . |
| 339009 | * 10/1989 | (EP) . |
| 0448070 | 9/1991 | (EP) . |
| 0461799 | 12/1991 | (EP) . |
| 0462721 | 12/1991 | (EP) . |
| 0516306 | 12/1992 | (EP) . |
| 2000973 | 1/1979 | (GB) . |
| 8800966 | 2/1988 | (WO) . |
| 9201383 | 2/1992 | (WO) . |
| 9409630 | 5/1994 | (WO) . |

OTHER PUBLICATIONS

ATCC Catalogue of Bacteria and Bacteriophages, 19th ed., 1996, p. 64.*
Bergey's Manual of Systematic Bacteriology, vol. 2, Sneath et al. ed., Williams and Wilkins, p. 1135, 1986.*
Levinson, et al., *J. Bacteriology*, 172(6):3172–3179 (1990).
Farkas. et al., *Chem. Commun.*, 42 (1977).
Aronson, et al., *Microbiol. Review*, 50(1):1–24 (1986).
Hofte, et al., *Microbiol. Reviews*, 53(2):242–255 (1989).
Sebesta, et al., *Micro. Contr. of Pests and Plant Diseases*, Acad. Press, N.Y., pp. 249–281 (1981).
He, et al., *Tetraqahedron Letters*, 35(16): 2499–2502 (1994).
Argauer, et al., *J. Entomol. Sci.*, 26(2): 205–213 (1991).
Gardner, W.A., *J. Economic Entomology*, 81(2):464–469 (1988).
Lüthy, P., *FEMS Microbiology Letters*, 8:1–7 (1980).
Salama, et al., *J. Appl. Ent.*, 101:304–313 (1986).
Chemical Abstracts, 101:124512s (1984).
Tailor, et al., *Molecular Microbiology*, 6(9):1211–1217 (1992).
Höfte, et al., *Microbiological Reviews*, 53(2):242–255 (1989).
Barton, et al., *Transgenic Plants*, 1:297–315.
Feitelson, et al., *Bio/Technology*, 10:271–275 (1992).
Balaraman, K., et al., *Indian J. Med. Res.*, 85(3):270–273 (1987).
Benz, G., *Experentia*, 31(11):1288–90 (1975).
Demain, et al., *Industrial Microbiology and Biotechnology*, ASM, 162–164 (1986).

* cited by examiner

Primary Examiner—Irene Marx
(74) Attorney, Agent, or Firm—Rockey, Milnamow & Kat,Lt (57) ABSTRACT

This invention is directed to a method for obtaining a factor which potentiates the pesticidal activity of a Bacillus related pesticide, a chemical pesticide and/or a virus with pesticidal properties.

9 Claims, 4 Drawing Sheets

FIG. 3 nOe's observed : 8.2 ⟶ 5.17
8.06 ⟶ 5.17, 5.34

METHODS FOR PRODUCING A POTENTIATOR OF BACILLUS PESTICIDAL ACTIVITY

This is a continuation of U.S. patent application Ser. No. 08/470,289, filed Jun. 6, 1995 now abandoned, which is a continuation-in-part application of application Ser. No. 08/295,323, filed Aug. 23, 1994, now abandoned, which is a continuation-in-part of application Ser. No. 08/146,852, filed Nov. 3, 1993 now abandoned, which is a continuation-in-part of application Ser. No. 08/095,240, filed Jul. 20, 1993, now abandoned, which is a continuation-in-part of application Ser. No. 07/990,202, filed Dec. 14, 1992, now abandoned, which is a continuation-in-part of application Ser. No. 07/971,786, filed Nov. 5, 1992 now abandoned.

1. FIELD OF THE INVENTION

The invention is related to a method of obtaining and identifying a factor which potentiates the pesticidal activity of a Bacillus related pesticide, a chemical pesticide and/or a virus with pesticidal properties.

2. BACKGROUND OF THE INVENTION

Every year, pests detrimental to agriculture, forestry, and public health cause losses in the millions of dollars. Various strategies have been used to control such pests.

One strategy is the use of chemical pesticides with a broad range or spectrum of activity. However, there are a number of disadvantages with using chemical pesticides. Specifically, because of their broad spectrum of activity, these pesticides may destroy non-target organisms such as beneficial insects and parasites of destructive pests. Additionally, chemical pesticides are frequently toxic to animals and humans. Furthermore, targeted pests frequently develop resistance when repeatedly exposed to such substances.

Another strategy involves the use of biopesticides to control insect, fungal and weed infestations. Biopesticides are naturally occurring pathogens and/or the substances produced bythese pathogens. The advantage of using biopesticides is that they are generally less harmful to non-target organisms and the environment as a whole compared to chemical pesticides.

2.1. Bacillus thuringiensis

The most widely used biopesticide is *Bacillus thuringiensis*. *Bacillus thuringiensis* is a motile, rod-shaped, gram-positive bacterium that is widely distributed in nature, especially in soil and insect-rich environments. During sporulation, *Bacillus thuringiensis* produces a parasporal crystal inclusion(s) which is insecticidal upon ingestion to susceptible insect larvae of the orders Lepidoptera, Diptera, and Coleoptera. The inclusions may vary in shape, number, and composition. They are comprised of one or more proteins called delta-endotoxins, which may range in size from 27–140 kDa. The insecticidal delta-endotoxins are generally converted by proteases in the larval gut into smaller (truncated) toxic polypeptides, causing midgut destruction, and ultimately, death of the insect (Höfte and Whiteley, 1989, *Microbiological Reviews* 53:242–255).

There are several *Bacillus thuringiensis* strains that are widely used as biopesticides in the forestry, agricultural, and public health areas. *Bacillus thuringiensis* subsp. *kurstaki* and *Bacillus thuringiensis* subsp. *aizawai* produce delta-endotoxins specific for Lepidoptera. A delta-endotoxin specific for Coleoptera is produced by *Bacillus thuringiensis* subsp. *tenebrionis* (Krieg et al., 1988, U.S. Pat. No. 4,766,203). Furthermore, *Bacillus thuringiensis* subsp. *israelensis* produces delta-endotoxins specific for Diptera (Goldberg, 1979, U.S. Pat. No. 4,166,112).

Other *Bacillus thuringiensis* strains specific for dipteran pests have also been described. A *Bacillus thuringiensis* isolate has been disclosed which is toxic to Diptera and Lepidoptera (Hodgman et al., 1993, *FEMS Microbiology Letters* 114:17–22). SDS polyacrylamide gel electrophoresis of the purified crystal delta-endotoxin from this isolate revealed three protein species which are related to CryIA(b), CryIB, and CryIIA toxins. There has also been disclosed a *Bacillus thuringiensis* isolate which produces a dipteran-active crystal comprised of proteins with molecular weights of 140, 122, 76, 72, and 38 kDa (Payne, 1994, U.S. Pat. No. 5,275,815). EPO 480,762 discloses five B.t. strains which are each active against dipteran pests; each also have a unique crystal delta-endotoxin pattern.

Several *Bacillus thuringiensis* strains have been described which have pesticidal activity against pests other then Lepidoptera, Coleoptera, and Diptera. Five *Bacillus thuringiensis* strains have been disclosed which produce delta-endotoxins that are toxic against nematodes (Edwards, Payne, and Soares, 1988, Eur. Pat. Appl. No. 0 303 426 B1). There has also been disclosed a *Bacillus thuringiensis* strain, PS81F, which can be used to treat humans and animals hosting parasitic protozoans (Thompson and Gaertner, 1991, Eur. Pat. Appl. No. 0 461 799 A2). Several *Bacillus thuringiensis* isolates have also been disclosed with activity against acaride pests. These isolates produce crystals comprised of proteins with molecular weights in the (wide) range of 35 kDa to 155 kDa (Payne, Cannon, and Bagley, 1992, PCT Application No. WO 92/19106). There have also been disclosed *Bacillus thuringiensis* strains with activity against pests of the order Hymenoptera (Payne, Kennedy, Randall, Meier, and Uick, 1992, Eur. Pat. Appl. No. 0 516 306 A2); with activity against pests of the order Hemiptera (Payne and Cannon, 1993, U.S. Pat. No. 5,262,159); with activity against fluke pests (Hickle, Sick, Schwab, Narva, and Payne, 1993, U.S. Pat. No. 5,262,399; and with activity against pests of the order Phthiraptera (Payne and Hickle, 1993, U.S. Pat. No. 5,273,746). Furthermore, another strain of *Bacillus thuringiensis* subsp. *kurstaki,* WB3S-16, isolated from Australian sheep wool clippings, has been disclosed that is toxic to the biting louse *Damalinia ovis,* a Phthiraptera pest (Drummond, Miller, and Pinnock, 1992,*J. Invert. Path.* 60:102–103).

The delta-endotoxins are encoded by cry (crystal protein) genes which are generally located on plasmids. The cry genes have been divided into six classes and several subclasses based on relative amino acid homology and pesticidal specificity. The major classes are Lepidoptera-specific (cryI); Lepidoptera-and Diptera-specific (cryII); Coleoptera-specific (cryIII); Diptera-specific (cryIV) (Höfte and Whiteley, 1989, *Microbiological Reviews* 53:242–255); Coleoptera- and Lepidoptera-specific (referred to as cryV genes by Tailor et al., 1992, *Molecular Microbiology* 6:1211–1217); and Nematode-specific (referred to as cryV and cryVI genes by Feitelson et al., 1992, *Bio/Technology* 10:271–275).

Delta-endotoxins have been produced by recombinant DNA methods. The delta-endotoxins produced by recombinant DNA methods may or may not be in crystal form.

Some strains of *Bacillus thuringiensis* have been shown to produce a heat-stable pesticidal adenine-nucleotide analog, known as β-exotoxin type I or thuringiensin, which is pesticidal alone (Sebesta et al., in H. D. Burges (ed.), *Microbial Control of Pests and Plant Diseases,* Academic Press, New York, 1980, pp. 249–281). β-exotoxin type I has been found in the supernatant of some *Bacillus thuringiensis* cultures. It has a molecular weight of 701 and is comprised of adenosine, glucose, and allaric acid (Farkas et al., 1977, *Coll. Czechosslovak Chem. Comm.* 42:909–929; Lüthy et al., in Kurstak (ed.), *Microbial and Viral Pesticides,* Marcel Dekker, New York, 1982, pp. 35–72). Its host range includes, but is not limited to, *Musca domestics, Mamestra configurata* Walker, *Tetranychus urticae, Drosophila melanogaster,* and *Tetranychus cinnabarinus.* The toxicity of β-exotoxin type I is thought to be due to inhibition of DNA-directed RNA polymerase by competition with ATP. It has been shown that S-exotoxin type I is encoded by a cry plasmid in five *Bacillus thuringiensis* strains (Levinson et al., 1990, *J. Bacteriol.* 172:3172–3179). β-exotoxin type I was found to be produced by *Bacillus thuringiensis* subsp. *thuringiensis* serotype 1, *Bacillus thuringiensis* subsp. *tolworthi* serotype 9, and *Bacillus thuringiensis* subsp. *darmstadiensis* serotype 10.

Another β-exotoxin classified as β-exotoxin type II has been described (Levinson et al., 1990, *J. Bacteriol.* 172:3172–3179). β-exotoxin type II was found to be produced by *Bacillus thuringiensis* subsp. *morrisoni* serotype 8ab and is active against *Leptinotarsa decemlineata.* The structure of β-exotoxin type II is not completely known, but is significantly different from that of β-exotoxin type I in that a pseudouridine moiety is in the place of adenine in which attachment to the ribose ring is at a position that would otherwise be occupied by a proton (Levinson, in Hickle and Finch (eds.), *Analytical Chemistry of Bacillus thuringiensis,* ACS Symposium Series, Washington, D.C., 1990, pp. 114–136). Furthermore, there is only one signal in the proton NMR spectrum corresponding to the nucleoside base (at 7.95 ppm), and does not have a ribose-type anomeric protein signal (5.78 ppm).

Other water soluble substances that have been isolated from *Bacillus thuringiensis* include alpha-exotoxin which is toxic against the larvae of Musca domestica (Luthy, 1980, *FEMS Microbial. Lett.* 8:1–7); gamma-exotoxins, which are various enzymes including lecithinases, chitinases, and proteases, the toxic effects of which are expressed only in combination with beta-exotoxin or delta-endotoxin (Forsberg et al., 1976, Bacillus thuringiensis: Its Effects on Environmental Quality, National Research Council of Canada, NRC Associate Committee on Scientific Criteria for Environmental Quality, Subcomittees on Pesticides and Related Compounds and Biological Phenomena); sigma exotoxin which has a structure similar to beta-exotoxin, and is also active against *Leptinotarsa decemlineata* (Argauer et al., 1991, *J. Entomol. Sci.* 26:206–213); and anhydrothuringiensin (Prystas et al., 1975, *Coll. Czechosslovak Chem. Comm.* 40:1775).

2.2. Zwittermicin

A substance has been isolated from *Bacillus cereus* which inhibits the growth of the plant pathogen *Phytophthora medicaginis* and reduces the infection of alfalfa (see, for example, U.S. Pat. Nos. 4,877,738 and 4,878,936). No other activity was disclosed. The following structure has been elucidated for zwittermicin A (He et al., Tet. Lett. 35:2499–2502):

3. OBJECTS OF THE INVENTION

The art has strived to achieve increased mortality of B.t. formulations. Means have included searching for new strains with increased mortality, attempting to engineer present strains, and attempting to design more effective formulations by combining B.t. spores and crystals with new pesticidal carriers chemical pesticides, or enhancers (see, for example, U.S. Pat. No. 5,250,515, a trypsin inhibitor). It is therefore an object of the present invention to potentiate the pesticidal activity of pesticides.

4. SUMMARY OF THE INVENTION

The invention relates to a method for obtaining which a factor which potentiates the pesticidal activity of a Bacillus related pesticide comprising (a) culturing a Bacillus strain under suitable conditions;

(b) recovering the factor from the supernatant of the culture of step (a).

In a specific embodiment, the Bacillus strain is selected from the group consisting of *Bacillus subtilus, Bacillus licheniformis,* and *Bacillus thuringiensis.* In a preferred embodiment, the factor is in substantially pure form. As defined herein a "substantially pure" factor means a factor which contains less than 10% of contaminants, for example, delta-endotoxin protein. Such a substantially pure factor may be obtained by isolating said factor, e.g., by column chromatography.

The factor obtained is a potentiator. As defined herein, a "potentiator" is a substance which has no significant pesticidal activity, e.g. having an $LC_{50}$ ($LC_{50}$ is the concentration of the substance required to kill 50% of the pests) of more than about 3000 µg/g as assayed by bioassay (see Section 6) but acts to increase the pesticidal activity of a Bacillus related pesticide at least about 50% and does not cause larval stunting. As noted in Section 2, other substances capable of enhancing pesticidal activity known in the art such as trypsin inhibitors and exotoxins have pesticidal activity.

In a specific embodiment, the factor is water soluble. As defined herein, a substance or compound is "water soluble" if at least about 1 mg of a substance can be dissolved in 1 ml of water. The factor may also potentiate the pesticidal activity of a chemical pesticide and/or a virus with pesticidal properties.

As defined herein, "a Bacillus related pesticide" is a Bacillus (e.g. *Bacillus thuringiensis* or *Bacillus subtilis*) strain, spore, or substance, e.g. protein or fragment thereof having activity against or which kill pests or a microorganism capable of expressing a Bacillus gene encoding a Bacillus protein or fragment thereof having activity against or which kill pests (e.g. *Bacillus thuringiensis* delta-endotoxin) and an acceptable carrier (see Section 5.2., infra, for examples of such carriers). The pest may be, for example, an insect, a nematode, a mite, or a snail. A microorganism capable of expressing a Bacillus gene encoding a Bacillus protein or fragment thereof having activity against or which kill pests inhabits the phylloplane (the surface of the plant leaves), and/or the rhizosphere (the soil surrounding plant roots), and/or aquatic environments, and is capable of successfully competing in the particular environment (crop and other insect habitats) with the wild-type microorganisms and provide for the stable maintenance and expression of a Bacillus gene encoding a Bacillus protein or fragment thereof having activity against or which kill pests. Examples of such microorganisms include but are not limited to bacteria, e.g. genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, Alcaligenes, and Clostridium; algae, e.g. families Cyanophyceae, Prochlorophyceae, Rhodophyceae, Dinophyceae, Chrysophyceae, Prymnesiophyceae, Xanthophyceae, Raphidophyceae, Bacillariophyceae, Eustigmatophyceae, Cryptophyceae, Euglenophyceae, Prasinophyceae, and Chlorophyceae; and fungi, particularly yeast, e.g. genera Saccharomyces, Cryptococcus, Kluyveromyces, Sporobolomyces, Rhodotorula, and Aureobasidium.

As defined herein, "pesticidal activity" measures the amount of activity against a pest through killing or stunting of the growth of the pest or protecting the plant from pest infestation.

The factor obtained may be formulated into a composition comprising the factor and a pesticidal carrier as well as the factor and a Bacillus related pesticide, chemical pesticide and/or a virus with pesticidal properties. These compositions may be used for controlling a pest, decreasing the resistance of a pest to a Bacillus related pesticide comprising exposing the pest to a composition comprising the factor and a pesticidally acceptable carrier, or potentiating the pesticidal activity of a Bacillus related pesticide.

The invention is also directed to a method for identifying said factor comprising
(a) culture of a strain of Bacillus;
(b) recovering the supernatant of the culture of (a); and
(c) assaying the supernatant of (b) for potentiation of a Bacillus related pesticide.

6. DETAILED DESCRIPTION OF THE INVENTION

The factor potentiates the pesticidal activity of a Bacillus related pesticide and may have a molecular weight of from about 350 to about 1200 or in a specific embodiment from about 350 to about 700.

The factor potentiates the pesticidal activity of a Bacillus related pesticide at least about 1.5 fold to optionally about 1000 fold, preferably from about 100 fold to about 400 fold. In a specific embodiment, the factor potentiates the pesticidal activity of a *Bacillus thuringiensis* delta-endotoxin including but not limited to a CryI (including but not limited to CryIA, CryIB, and CryIC), CryII, CryIII, CryIV, CryV, or CryVI protein in full-length form or a proteolytically processed, truncated form, from about 1.5 fold to about 1000 fold. In a most specific embodiment, the factor potentiates a B.t. delta-endotoxin from about 100 fold to about 400 fold. The factor may also potentiate the pesticidal activity of a chemical pesticide and/or a virus with pesticidal properties.

The factor may also be water soluble, stable in water up to about 100° C. for at least about 5 minutes, stable when subjected to direct sunlight for at least about 10 hours, and/or stable at a pH of about 2 for about 10 days. The factor may have 13 carbons. Additionally, the factor may have $^1$H NMR shifts at δ1.5, 3.22, 3.29, 3.35, 3.43, 3.58, 3.73, 3.98, 4.07, 4.15, 4.25, 4.35.

In a most specific embodiment, said factor has the structure Ia or salt thereof.

The salt would be capable of potentiating a Bacillus related pesticide.

6.1. Obtaining the Factor

The factor may be obtainable from a Bacillus strain (e.g. *Bacillus subtilis, Bacillus licheniformis,* and *Bacillus thuringiensis*) in shake flasks or a fermentor. In a specific embodiment, the factor is obtainable from the supernatant of a *Bacillus thuringiensis* culture including but not limited to *Bacillus thuringiensis* subsp. *kurstaki, Bacillus thuringiensis* subsp. *aizawai, Bacillus thuringiensis* subsp. *galleriae, Bacillus thuringiensis* subsp. *entomocidus, Bacillus thuringiensis* subsp. *tenebrionis, Bacillus thuringiensis* subsp. *thuringiensis, Bacillus thuringiensis* subsp. *alesti, Bacillus thuringiensis* subsp. *canadiensis, Bacillus thuringiensis* subsp. *darmstadiensis, Bacillus thuringiensis* subsp. *dendrolimus, Bacillus thuringiensis* subsp. finitimus, *Bacillus thuringiensis* subsp. *kenyae, Bacillus thuringiensis* subsp. *morrisoni, Bacillus thuringiensis* subsp. *subtoxicus, Bacillus thuringiensis* subsp. *toumanoffi* and *Bacillus thuringiensis* subsp. *israelensis.* In a preferred embodiment, the factor is obtainable from the supernatant of *Bacillus thuringiensis* subsp. *kurstaki, Bacillus thuringiensis* subsp. *aizawai,* or *Bacillus thuringiensis* subsp. galleriae or mutants thereof having substantially the same potentiating activity. In a specific embodiment, the factor is recovered from a cry- spo-mutant of *Bacillus thuringiensis* subsp. *kurstaki.*

Bacillus may be cultured using media and fermentation techniques known in the art (see, for example, Rogoff et al., 1969, J. Invertebrate Path. 14:122–129; Dulmage et al., 1971, J. Invertebrate Path. 18:353–358; Dulmage et al., in Microbial Control of Pests and Plant Diseases, H. D. Burges, ed., Academic Press, N.Y., 1980). Upon completion of the cycle, the supernatant can be recovered by separating B.t. spores and crystals from the culture (fermentation) broth by means well known in the art, e.g. centrifugation and/or ultrafiltration. The factor is contained in the supernatant which may be recovered by means well known in the art, e.g. ultrafiltration, evaporation, and spray-drying. This procedure is more specifically described in the sections which follow.

Purification of the factor can be carried out by various procedures known in the art, including but not limited to chromatography (e.g. ion exchange, affinity, and size exclusion column chromatography), electrophoretic procedures, differential solubility, extraction, or any other standard technique known in the art.

The potentiating activity of the factor of the pesticidal activity of Bacillus related pesticide, virus having pesticidal activity, or chemical pesticide against various pests may be assayed using procedures known in the art, such as an artificial insect diet incorporated, artificial diet overlay, leaf painting, leaf dip, and foliar spray. Specific examples of such assays are given in Section 7, infra.

6.2. Compositions Comprising the Factor

The factor obtained can be formulated alone; with a Bacillus related pesticide, which as defined, supra, is a Bacillus strain, spore, protein or fragment, or other substance, thereof, with activity against or which kills pests or protects plants against a pest; with a chemical pesticide and/or an entomopathogenic virus and an acceptable carrier into a pesticidal composition(s), that is, for example, a suspension, a solution, an emulsion, a dusting powder, a dispersible granule, a wettable powder, an emulsifiable concentrate, an aerosol or impregnated granule. Examples of such Bacillus strains include, but are not limited to, *Bacillus thuringiensis* subsp. *kurstaki* (marketed as DIPEL™ from Abbott Laboratories, Inc., JAVELIN™ from Sandoz, BIO-BIT™ from Novo Nordisk A/S, FORAY™ from Novo Nordisk A/S, BIOCOT™ from Novo Nordisk A/S, MVP™ from Mycogen, BACTOSPEINE™ from Novo Nordisk A/S, and THURICIDE™ from Sandoz); *Bacillus thuringiensis* subsp. *aizawai* (marketed as FLORBAC™ from Novo Nordisk A/S, and XENTARI™ from Abbott Laboratories, Inc.); *Bacillus thuringiensis* subsp. *tenebrionis* (marketed as NOVODOR™ from Novo Nordisk A/S, TRIDENT™ from Sandoz, and M-TRAK™ and M-ONE™ from Mycogen); *Bacillus thuringiensis* subsp. *israelensis* (marketed as either BACTIMOS™ or SKEETAL™ from Novo Nordisk A/S, TEKNAR™ from Sandoz, and VECTOBAC™ from Abbott Laboratories, Inc.); *Bacillus thuringiensis kurstaki/tenebrionis* (marketed as FOIL™ from Ecogen); *Bacillus thuringiensis kurstaki/aizawai* (marketed as CONDOR™ from Ecogen and AGREE™ from Ciba-Geigy); and *Bacillus thuringiensis kurstaki/kurstaki* (marketed as CUTLASS™ from Ecogen). The Bacillus related protein may be selected from the group including, but not limited to, CryI, CryII, CryIII, CryIV, CryV, and CryVI. The chemical pesticide may be, for example, an insect growth regulator such as diflubenzuron, a carbamate such as thiodicarb and methomyl, an organophosphate such as chlorpyrifos, a pyrethroid such as cypermethrin and esfenvalerate, inorganic fluorine such as cryolite, and a pyrrole. The entomopathogenic virus may be a baculovirus, e.g., *Autographa californica* nuclear polyhedrosis virus (NPV), *Syngrapha falcifera* NPV, *Cydia pomonella* GV (granulosis virus), *Heliothis zea* NPV, *Lymantria dispar* NPV, *Orgyia pseudotsugata* NPV, *Spodoptera exigua* NPV, *Neodiprion lecontei* NPV, *Neodiprion sertifer* NPV, *Harrisina brillians* NPV, and *Endopiza viteana* Clemens NPV.

In compositions comprising the substance and a Bacillus related pesticide, the substance may be present in the amount of at least about 0.1 g/BIU or 0.05 g factor per g Bacillus delta-endotoxin and spore, optionally to about 300 g/BIU or 150 g substance per g Bacillus delta-endotoxin and spore, preferably 2 g/BIU or 1 g substance per g Bacillus delta-endotoxin and spore. As defined herein "BIU" is billion international units as determined by bioassay. The bioassay compares the sample to a standard Bacillus reference material using *Trichoplusia ni* or other pest as the standard test insect. The potency is determined by dividing the reference standard $LC_{50}$ then multiplying by the reference standard potency.

In another embodiment, the composition may comprise the factor in substantially pure form or a supernatant from Bacillus in dry, concentrated, or liquid form and a pesticidally acceptable carrier, examples of which are disclosed, infra. This composition may be applied separately to a plant, e.g., transgenic plants. Specifically, the composition may be applied to a plant previously containing and expressing a *Bacillus thuringiensis* gene. In another embodiment, the composition may be applied to a plant previously exposed to a *Bacillus thuringiensis* composition. In another embodiment, the composition may be applied to other environments of a dipteran pest(s), e.g., water or soil. The substance is present in the composition at a concentration of about 0.001% to about 60% (w/w).

The composition comprising the substance and a pesticidally acceptable carrier in addition to controlling a pest may also be used to decrease the resistance of a pest to a pesticide. Alternatively, the composition may be used to potentiate a Bacillus related pesticide. The composition in one embodiment may be applied at the same time as the pesticide in an amount of at least about 2 g substance/BIU up to optionally about 300 g substance/BIU. In another embodiment, the composition may be applied up to about 24 hours after the pesticide as an adjuvant to extend the efficacy of residual pesticide.

Such compositions disclosed above may be obtained by the addition of a surface active agent, an inert carrier, a preservative, a humectant, a feeding stimulant, an attractant, an encapsulating agent, a binder, an emulsifier, a dye, a U.V. protectant, a buffer, a flow agent, or other component to facilitate product handling and application for particular target pests.

Suitable surface-active agents include anionic compounds such as a carboxylate, for example, a metal carboxylate of a long chain fatty acid; a N-acylsarcosinate; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl-naphthalene sulphonate; salts or sulphonated naphthalene-formaldehyde condensates; salts of sulphonated phenol-formaldehyde condensates; or more complex sulphonates such as the amide sulphonates, e.g., the sulphonated condensation product of oleic acid and N-methyl taurine or the dialkyl sulphosuccinates, e.g., the sodium sulphonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine as an acetate, naphthenate or oleate; an oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include inorganic minerals such as kaolin, mica, gypsum, fertilizer, phyllosilicates, carbonates, sulfates, or phosphates; organic materials such as sugar, starches, or cyclodextrins; or botanical materials such as wood products, cork, powdered corncobs, rice hulls, peanut hulls, and walnut shells.

The compositions of the present invention can be in a suitable form for direct application or as a concentrate or primary composition which requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50%, preferably 0.1 to 50% of a surfactant. These compositions will be administered at the labeled rate for the commercial product, preferably about 0.01 pound to 5.0 pounds per acre when in dry form and at about 0.01 pint to 25 pints per acre when in liquid form.

In a further embodiment, the *Bacillus thuringiensis* crystal delta-endotoxin and/or factor can be treated prior to formulation to prolong the pesticidal activity when applied to the environment of a target pest as long as the pretreatment is not deleterious to the crystal delta-endotoxin or substance. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropranol and ethanol; and histological fixatives, such as Bouin's fixative and Helly's fixative (see, for example, Humason, *Animal Tissue Techniques,* W.H. Freeman and Co., 1967).

The compositions of the invention can be applied directly to the plant by, for example, spraying or dusting at the time when the pest has begun to appear on the plant or before the appearance of pests as a protective measure. Plants to be protected within the scope of the present invention include, but are not limited to, cereals (wheat, barley, rye, oats, rice, sorghum and related crops), beets (sugar beet and fodder beet), drupes, pomes and soft fruit (apples, pears, plums, peaches, almonds, cherries, strawberries, raspberries, and blackberries), leguminous plants (alfalfa, beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages and other brassicae, carrots, onions, tomatoes, potatoes), lauraceae (avocados, cinnamon, camphor), deciduous trees and conifers (linden-trees, yew-trees, oak-trees, alders, poplars, birch-trees, firs, larches, pines), or plants such as maize, turf plants, tobacco, nuts, coffee, sugar cane, tea, vines, hops, bananas and natural rubber plants, as well as ornamentals. The composition can be applied by foliar, furrow, broadcast granule, "lay-by", or soil drench application. It is generally important to obtain good control of pests in the early stages of plant growth as this is the time when the plant can be most severely damaged. The spray or dust can conveniently contain another pesticide if this is thought necessary. In a preferred embodiment, the composition of the invention is applied directly to the plant.

The compositions of the present invention can also be applied directly to ponds, lakes, streams, rivers, still water, and other areas subject to infestation by dipteran pests, especially pests of concern to public health. The composition can be applied by spraying, dusting, springling, or the like.

The compositions of the present invention may be effective against insect pests of the order Lepidoptera, e.g., *Achroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis,* Archips sp., Argyrotaenia sp., *Athetis mindara, Bombyx mori, Bucculatrix thurberiella, Cadra cautella,* Choristoneura sp., *Cochylis hospes, Colias eurytheme, Corcyra cephalonica, Cydia latiferreanus, Cydia pomonella, Datana integerrima, Dendrolimus sibericus, Desmia funeralis, Diaphania hyalinata, Diaphania nitidalis, Diatraea grandiosella, Diatraea saccharalis, Ennomos subsignaria, Eoreuma loftini, Ephestia elutella, Erannis tiliaria, Estigmene acrea, Eulia salubricola, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantria cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrsisalis,* Malacosoma sp., *Mamestra brassicae, Mamestra configurata, Manduca quinquemaculata, Manduca sexta, Maruca testulalis, Melanchra picta, Operophtera brumata,* Orgyia sp., *Ostrinia nubilalis, Paleacrita vernata, Papilio cresphontes, Pectinophora gossypiella, Phryganidia califormica, Phyllonorycter blancardella, Pieris napi, Pieris rapae, Plathypena scabra, Platynota flouendana, Platynota sultana, Platyptilia carduidactyla, Plodia interpunctella, Plutella xylostella, Pontia protodice, Pseudaletia unipuncta, Pseudoplusia includens, Sabulodes aegrotata, Schizura concinna, Sitotroga cerealella, Spilonota ocellana,* Spodoptera sp., *Thaurnstopoea pityocampa, Tineola bisselliella, Trichoplusia ni, Udea rubigalis, Xylomyges curialis, Yponomeuta padella;* order Diptera, e.g., Aedes sp., *Andes vittatus, Anastrepha ludens, Anastrepha suspensa, Anopheles barberi, Anopheles quadrimaculatus, Armigeres subalbatus, Calliphora stygian, Calliphora vicina, Ceratitis capitata, Chironomus tentans, Chrysomya rufifacies, Cochliomyia macellaria,* Culex sp., *Culiseta inornata, Dacus oleae, Delia antiqua, Delia platura, Delia radicum, Drosophila melanogaster, Eupeodes corollae, Glossina austeni, Glossina brevipalpis, Glossina fuscipes, Glossina morsitans centralis, Glossina morsitans morsitans, Glossina moristans submorsitans, Glossina pallidipes, Glossina palpalis gambiensis, Glossina palpalis palpalis, Glossina tachinoides, Haemagogus equinus, Haematobia irritans, Hypoderma bovis, Hypoderma lineatum, Leucopis ninae, Lucilia cuprina, Lucilia sericata, Lutzomyia longlpaipis, Lutzommyia shannoni, Lycoriella mali, Mayetiola destructor, Musca autumnalis, Musca domestica, Neobellieria* sp., *Nephrotoma suturalis, Ophyra aenescens, Phaenicia sericata,* Phlebotomus sp., *Phormia regina, Sabethes cyaneus, Sarcophaga bullata, Scatophaga stercoraria, Stomoxys calcitrans, Toxorhynchites amboinensis, Tripteroides bambusa.* However, the compositions of the invention may also be effective against insect pests of the order Coleoptera, e.g., Leptinotarsa sp., *Acanthoscelides obtectus, Callosobruchus chinensis, Epilachna varivestis, Pyrrhalta luteola, Cylas formicarius elegantulus, Listronotus oregonensis,* Sitophilus sp., *Cyclocephala borealis, Cyclocephala immaculata, Macrodactylus subspinosus, Popillia japonica, Rhizotrogus majalis, Alphitobius diaperinus, Palorus ratzeburgi, Tenebrio molitor, Tenebrio obscurus, Tribolium castaneum, Tribolium confusum, Tribolius destructor;* Acari, e.g., *Oligonychus pratensis, Panonychus ulmi, Tetranychus urticae;* Hymenoptera, e.g., *Iridomyrmex humilis, Solenopsis invicta;* Isoptera, e.g., *Reticulitermes hesperus,*

*Reticulitermes flavipes, Coptotermes formosanus, Zootermopsis angusticollis, Neotermes connexus, Incisitermes minor, Incisitermes immigrans;* Siphonaptera, e.g., *Ceratophyllus gallinae, Ceratophyllus niger, Nosopsyllus fasciatus, Leptopsylla segnis, Ctenocephalides canis, Ctenocephalides felis, Echicnophaga gallinacea, Pulex irritans, Xenopsylla cheopis, Xenopsylla vexabilis, Tunga penetrans;* and Tylenchida, e.g., *Melodidogyne incognita, Pratylenchus penetrans.*

The following examples are presented by way of illustration, not by way of limitation.

7. EXAMPLE

Characterization of Ia

As detailed herein, Ia is recovered and purified. The characterization of Ia is detailed infra.

7.1. Recovery and Purification of Ia

*B. thuringiensis* subsp. *kurstaki* strain EMCC0086 (NB75 deposited with the NRRL as B-21147) is fermented for 72 hours at 30° C. in a medium comprised of a carbon source such as starch, hydrolyzed starch, or glucose and a nitrogen source such as protein, hydrolyzed protein, or corn steep liquor. The production of Ia is detected at 13 hours into the fermentation. Peak activity is found to be at approximately 30 hours.

Supernatant from a *B. thuringiensis* subsp. *kurstaki* fermentation is recovered by centrifugation and then is clarified by ultrafiltration through a 30 kDa MW-CO membrane using a Rhone Poulenc UF system. The 30 kDa filtration removed any remaining cell debris, crystal delta-endotoxin, spores, and soluble protein greater than 30 kDa molecular mass. The permeate is concentrated 10 fold by evaporation. The permeate is centrifuged and then 0.2$\mu$ filtered to further remove insolubles from the broth, leaving a clear broth containing Ia.

Figure 1:
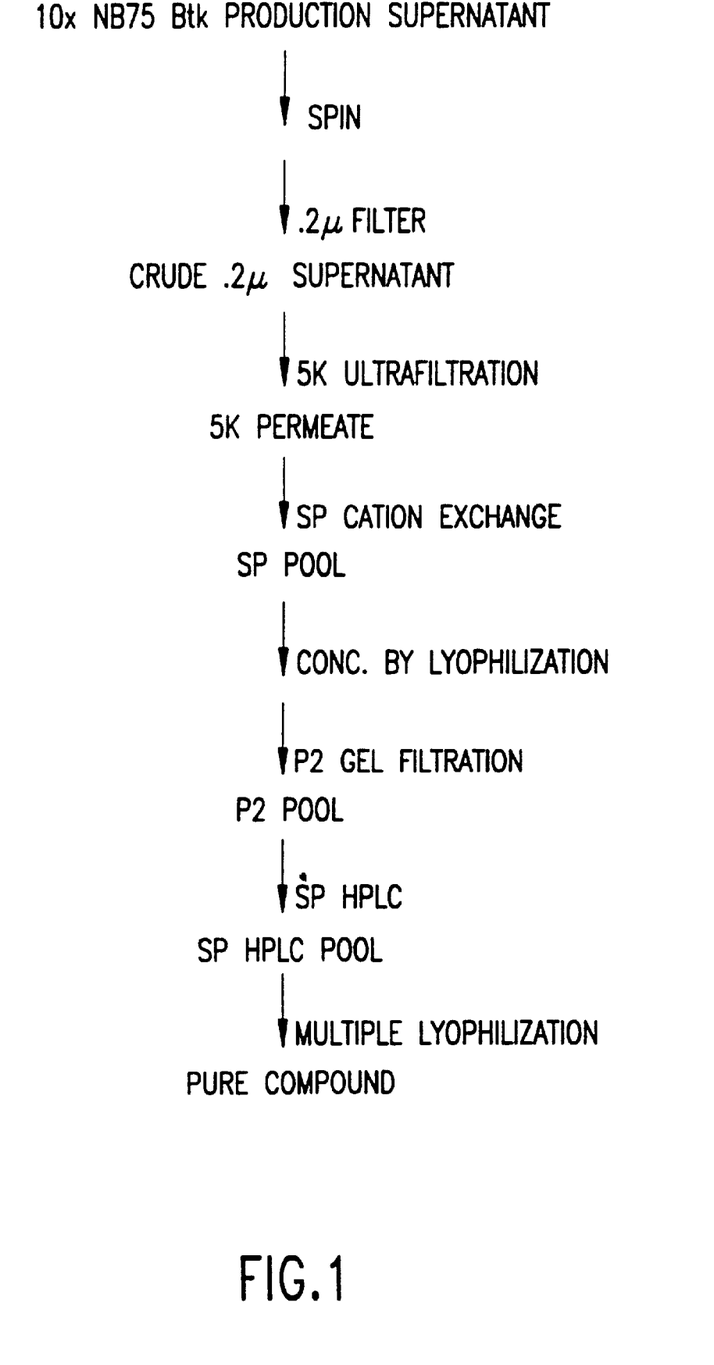
FIG. 1 schematically shows the general procedure used for purifying Ia.

The purification of Ia to homogeneity is achieved using a multi-step purification procedure shown schematically in FIG. 1. In conjunction with the recovery protocol outlined above, the purification proceeded with a 5 kDa ultrafiltration step. The permeate from the 5 kDa ultrafiltration is adsorbed to a Sulfopropyl (SP) cation exchange resin and eluted with an ammonium acetate solution. The compound is then concentrated approximately 30× by lyophilization, and the salt and other contaminants are removed with a BioRad P2 size exclusion column. The pool from the P2 column is run over a high resolution SP HPLC cation exchange column which yielded a homogeneous compound. The contaminating salt is removed by repeated lyophilization.

Activity is monitored by a Spodoptera exigua microbioassay, and purity is determined by capillary electrophoresis. Sample consisting of 50 $\mu$l of Ia and 50 $\mu$l of CryIA(c) protein (15 $\mu$g/ml) purified from BIOBIT™ FC (100 $\mu$l), is applied to individual wells of a jelly tray containing 500 $\mu$l of solidified artificial insect diet. The trays containing the various samples are air dried. Two to four 2nd or early 3rd instar *Spodoptera exigua* are added to the wells containing the dried sample. The wells are sealed with mylar poked with holes and are incubated for 2–3 days at 30° C. Degree of stunting and percent mortality are then recorded. Typically, 5 replicate wells are run for each sample.

7.2. Structure Elucidation

Figure 2:
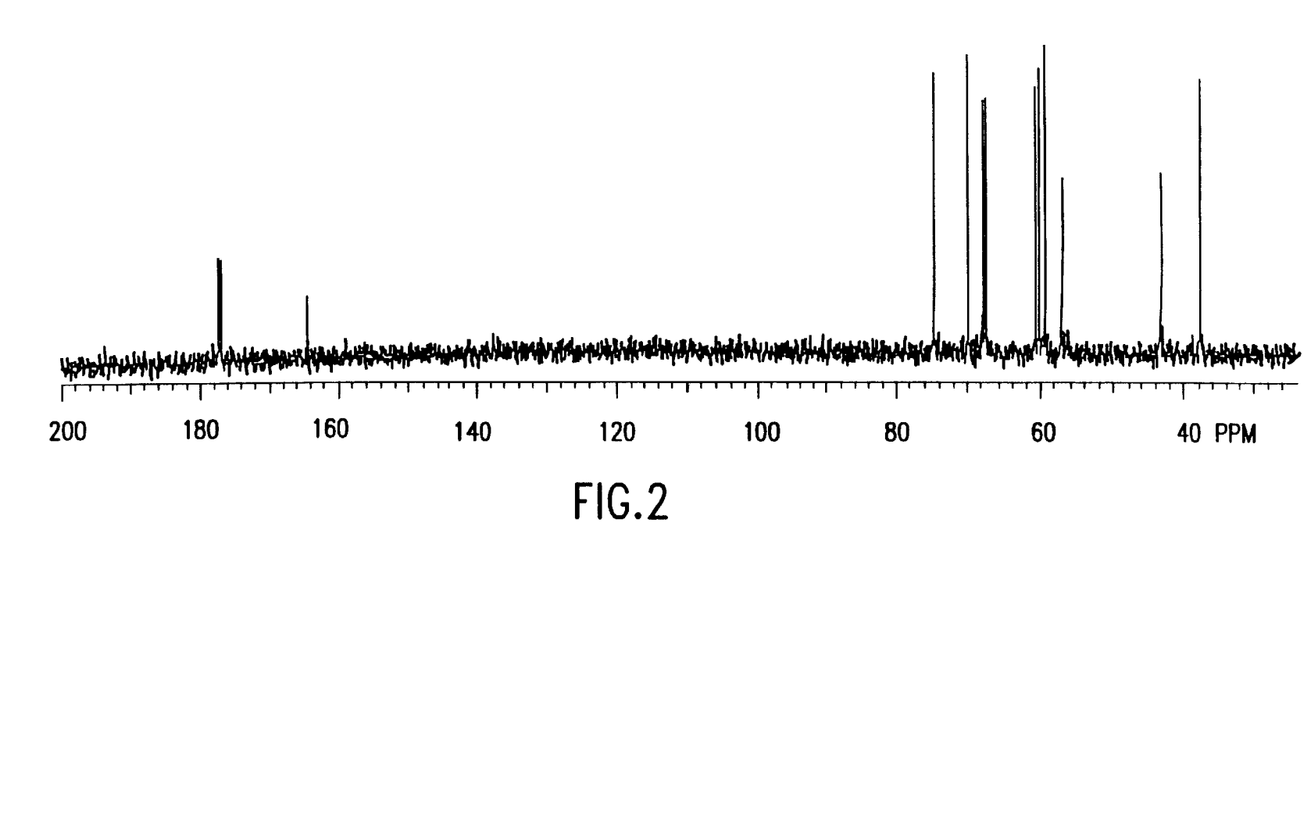
FIG. 2 shows the $^{13}$C NMR spectrum of Ia.
Figure 3:
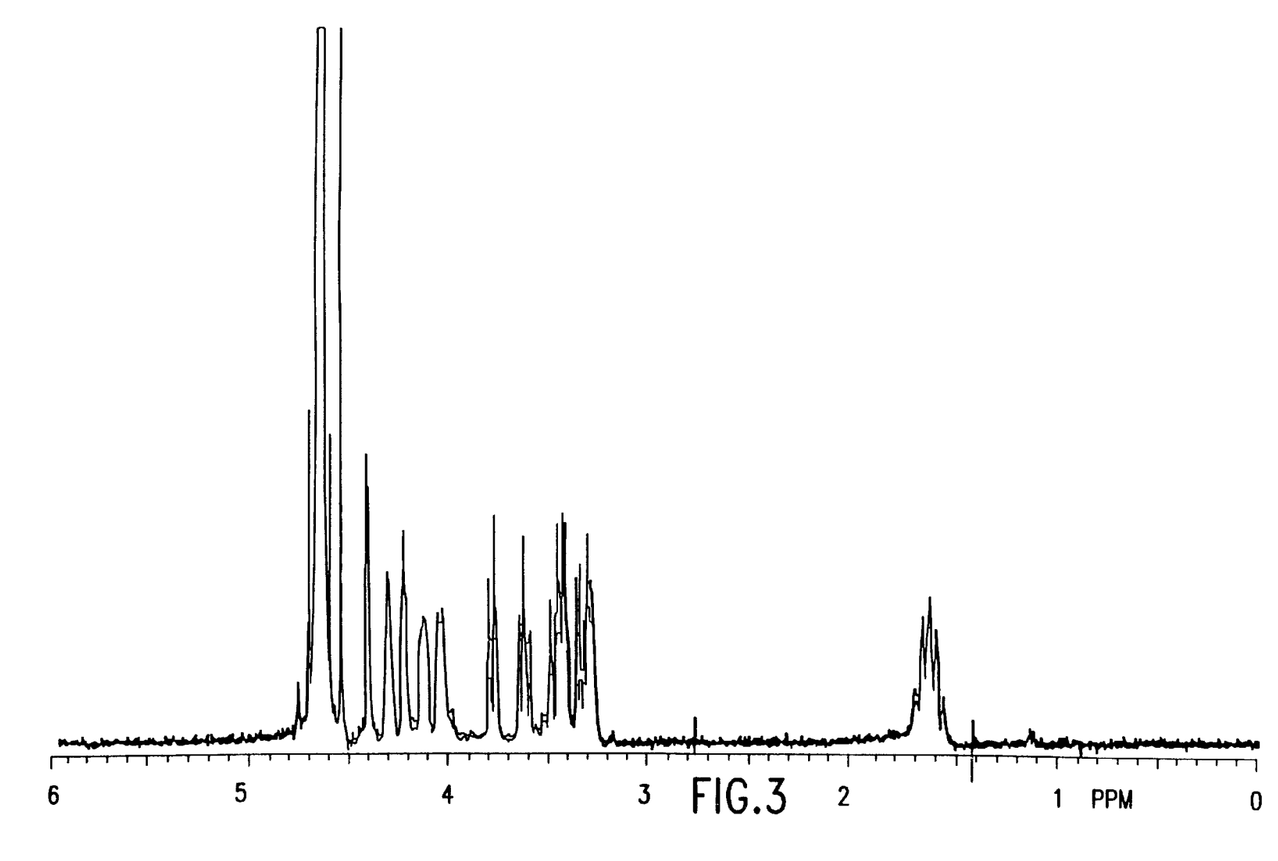
FIG. 3 shows the proton NMR spectrum of Ia.

The active compound is found to be water soluble but is not soluble in organic solvents. It is positively charged and reacted with ninhydrin as evidenced by silica thin layer chromatography. 13C and proton NMR of the compound are shown in FIGS. 2 and 3, respectively. $^{13}$C NMR experiments revealed the presence of 13 carbons (referenced to 3-[trimethylsilyl propionic acid). A DEPT experiment determined that there are three quaternary carbons (C), seven methines (CH), three methylenes ($CH_2$) and no methyl groups ($CH_3$). Using proton coupling experiments such as 1-D decoupling and COSY, one large spin system containing eight carbons is identified. In addition, a smaller spin system consisting of two carbons is present. A carbon proton correlation experiment (HMBC) enabled assignment of each proton resonance in the molecule to its attached carbon.

Treatment of the active compound (13 mg) with acetic anhydride in pyridine resulted in the formation of an acetylated derivative which is much less polar. This derivative is purified by HPLC to give 3 mg of pure acetylated derivative. Mass spectroscopy analysis revealed that the derivative has 7 acetates and a molecular weight of 690, which gives a molecular weight of 396 for the active compound and indicates that an even number of nitrogens are present. Also, fragments containing 6 acetates and 5 acetates are detected. High resolution data for 5 and 6 acetate daughter ions are 645.2594 (6 acetates) and 607.2519 (5 acetates) which indicate the following molecular formula for Ia, $C_{13}H_{28}N_6O_8$.

Treatment of the active compound (13 mg) with 6 N HCl gave a derivative which is ninhydrin positive. These results indicate the presence of amide bonds. The derivative had the same $R_f$ value as determined by thin layer chromatography as 2,3-diaminopropionic acid. These results along with NMR data, suggest the presence of 2,3 diaminopropionic acid.

Figure 4:
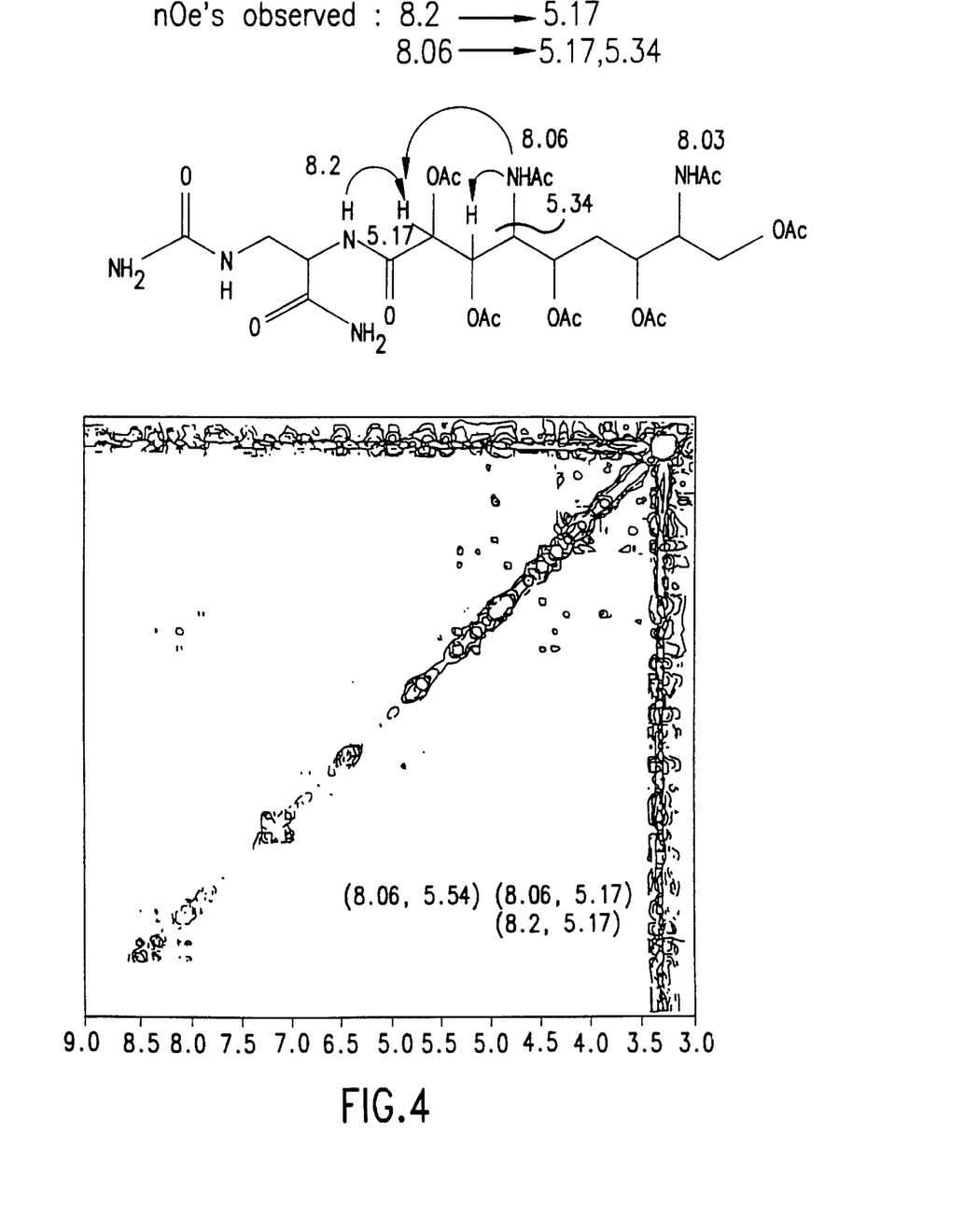
FIG. 4 shows the results of nOe experiments on the acetylated derivative of Ia.

Another technique used to analyzed Ia is nOe (Nuclear Overhauser Effect) which can detect proximity of protons to one another through space. nOe is carried out on an acetylated derivative of Ia. In a two dimensional nOe experiment (NOESY), NOEs are observed between an N—H proton at 8.06 ppm and the 5.17 proton (FIG. 4).

The following structure has been elucidated for Ia

It can be classified as a ureido amide. Constituents include 2 amides, a urea, two aminos, and five hydroxyls. It contains seven chiral centers.

7.3. Properties of Ia

The isolated Ia is found to potentiate the activity of *Bacillus thuringiensis* subsp. *kurstaki* and *Bacillus thuringiensis* subsp. *aizawai* crystal delta-endotoxin pesticidal proteins toward *Spodoptera exigua* regardless of the form of the pesticidal proteins. The pesticidal activity of formulated B.t.k., isolated crystals, full-length (130 kDa molecular mass) or truncated CryIA proteins (~65 kDa molecular mass) are all potentiated. The activity of CryII and CryIC inclusions are also potentiated. It is also found to potentiate the activity of the individual truncated CryIA(a), (b), and (c) proteins. Incubation time of Ia with the Cry protein is not found to be critical for bioactivity. However, Ia is inactive alone. The level of potentiation is found to be 100–200 fold for the truncated CryIA proteins, CryII and CryIC inclusions and approximately 320 fold with full-length CryIA(c) (see Tables I and II respectively). Specifically, for full-length protein, 0.75 $\mu$g/ml CryIA(c) produced the same insect mortality/stunt score when Ia is included as 240 $\mu$g/ml of CryIA(c) alone. In the case of the truncated CryIA(c), an $OD_{280}$ of 0.0006 gave the same stunt score in combination with Ia as the same sample of CryIA(c) tested alone with an $OD_{280}$ of 0.075. CryII inclusions, at a concentration of 0.6 μg/ml gave the same stunt score and similar mortality in combination with Ia as CryII protein alone at 75 μg/ml, a 125 fold potentiation. CryIC inclusions, at 0.3 μg/ml with the addition of Ia gave similar mortality and stunt score as 75 μg/ml of the CryIC protein alone, which reflects a 250 fold level of potentiation. The concentration of CryIA protein that produced stunting yielded mortality on addition of Ia.

Ia is found to be stable by bioassay as described in Section 7.1. upon boiling for 5 minutes, but loses all activity upon autoclaving (>190C). Further, it is stable when subjected to direct sunlight for at least 10 hours. Ia is stable at pH 2 for 3 days, but unstable at pH 12. It is found to lose all activity when exposed to periodic acid or concentrated HCl.

TABLE I

POTENTIATION EFFECTS
OF Ia WITH PURIFIED TRUNCATED Bt PROTEIN

| Bt Protein | | Spodoptera Exigua | |
|---|---|---|---|
| Type | OD280 | Ia | Mortality* | Stunt Score† |
| CryIa(a) | 0.055 | − | 0/5 | 2.2 |
| | 0.040 | − | 0/5 | 2.2 |
| | 0.020 | − | 0/5 | 2.0 |
| | 0.020 | + | 2/5 | 0.0 |
| | 0.010 | + | 0/5 | 0.2 |
| | 0.005 | + | 0/5 | 0.0 |
| | 0.0025 | + | 0/5 | 0.4 |
| | 0.0012 | + | 0/5 | 1.8 |
| | 0.0006 | + | 0/5 | 1.6 |
| CryIA(c) | 0.075 | − | 0/5 | 3.4 |
| | 0.040 | − | 0/5 | 2.6 |
| | 0.020 | − | 0/5 | 2.8 |
| | 0.020 | + | 1/5 | 0.0 |
| | 0.010 | + | 0/5 | 0.2 |
| | 0.005 | + | 1/5 | 0.0 |
| | 0.0025 | + | 2/5 | 2.0 |
| | 0.0012 | + | 0/5 | 1.0 |
| | 0.0006 | + | 1/5 | 1.0 |
| None | NA | + | 0/5 | 4.0 |
| None | NA | − | 0/5 | 4.0 |

*Mortality = # insects dead/# total insects after 2 days
†Stunt score is defined by the average size of the live insect larvae at the end of the bioassay: 4.0 = untreated control, 3.0 = 75% size of untreated control, 2.0 = 50% size of untreated control, 1.0 = 25% size of untreated control, 0.0 = no growth or size unchanged from start of experiment.

TABLE II

POTENTIATION EFFECTS OF Ia WITH Bt PROTEIN

| Bt Protein | | Spodoptera Exigua | |
|---|---|---|---|
| Type | μg/ml | Ia | Mortality* | Stunt Score† |
| CryIA(c) | 240 | − | 1/5 | 0.5 |
| | 120 | − | 0/5 | 2.2 |
| | 60 | − | 0/5 | 2.2 |
| | 30 | − | 0/5 | 4.0 |
| | 60 | + | 5/5 | — |
| | 30 | + | 5/5 | — |
| | 15 | + | 4/5 | 0.0 |
| | 3 | + | 4/5 | 1.0 |
| | 0.8 | + | 2/5 | 1.6 |
| CryII | 300 | − | 1/5 | 0.8 |
| | 150 | − | 2/5 | 0.7 |
| | 75 | − | 1/5 | 0.2 |
| | 38 | − | 0/5 | 0.8 |
| | 19 | − | 0/5 | 1.6 |
| | 9 | − | 0/5 | 1.8 |
| | 5 | − | 1/5 | 4.0 |
| | 38 | + | 3/5 | 1.0 |

TABLE II-continued

POTENTIATION EFFECTS OF Ia WITH Bt PROTEIN

| Bt Protein | | Spodoptera Exigua | |
|---|---|---|---|
| Type | μg/ml | Ia | Mortality* | Stunt Score† |
| | 19 | + | 2/5 | 0.5 |
| | 9 | + | 3/5 | 0.0 |
| | 5 | + | 1/5 | 0.5 |
| | 2.4 | + | 1/5 | 0.0 |
| | 1.2 | + | 3/5 | 0.5 |
| | 0.6 | + | 2/5 | 0.3 |
| CryII | 300 | − | 2/5 | 0.3 |
| | 150 | − | 2/5 | 0.0 |
| | 75 | − | 1/5 | 0.8 |
| | 38 | − | 0/5 | 3.2 |
| | 38 | + | 5/5 | — |
| | 19 | + | 5/5 | — |
| | 9 | + | 5/5 | — |
| | 5 | + | 4/5 | 0.0 |
| | 2.4 | + | 1/5 | 0.0 |
| | 1.2 | + | 5/5 | — |
| | 0.6 | + | 3/5 | 1.5 |
| | 0.3 | + | 2/5 | 1.3 |
| None | NA | − | 0/5 | 4.0 |
| None | NA | + | 0/5 | 4.0 |

*Mortality = # insects dead/# total insects after 2 days
†Stunt score is defined by the average size of the live insect larvae at the end of the bioassay: 4.0 = untreated control, 3.0 = 75% size of untreated control, 2.0 = 50% size of untreated control, 1.0 = 25% size of untreated control, 0.0 = no growth or size unchanged from start of experiment.

7.4. Evaluation of Other Subspecies of *Bacillus thurinaiensis* and Other Species of Bacilli Several Bacillus species are evaluated for production of Ia. The strains are fermented for 72 hours at 30° C. in a medium comprised of a carbon source such as starch, hydrolyzed starch, or glucose and a nitrogen source such protein, hydrolyzed protein, or corn steep liquor. The supernatants are tested for Ia production using the Spodoptera exigua micro-bioassay described supra. *B. thuringiensis* subsp. *aizawai* strain EMCC0087 (deposited with the NRRL as NRRL B-21148) and *B. thuringiensis* subsp. *galleriae* (deposited with the NRRL) are found to produce Ia in about the same concentration as *B. thuringiensis* subsp. *kurstaki*.

Ia is also produced in *B. subtilis, B. cereus,* B.t. subsp. *alesti,* B.t. subsp. *canadiensis,* B.t. subsp. *darmstadiensis,* B.t. subsp. *dendrolimus,* B.t. subsp. *entomocidus,* B.t. subsp. *finitimus,* B.t. subsp. *israelensis,* B.t. subsp. *kenyae,* B.t. subsp. *morrisoni,* B.t. subsp. *subtoxicus,* B.t. subsp. *tenebrionis,* B.t. subsp. *thuringiensis,* and B.t. subsp. *toumanoffi, B. cereus, B. subtilis,* and *B. thuringiensis* subsp. *kurstaki* cry- spo-mutant as determined by capillary electrophoresis.

Specifically, a Beckman P/ACE Capillary Electrophoresis System equipped with a 50 μm×57 cm uncoated capillary, 0.2 M phosphate pH 6.8 buffer, voltage at 15KV, and detection at 200 nm is used for quantifying the level of Ia. Sample volumes are 20 nl with a run time of 25 minutes.

A standard curve is generated using purified Ia as the standard at levels of 1.25 mg/ml, 0.625 mg/ml, 0.3125 mg/ml, 0.156 mg/ml, and 0.078 mg/ml. A linear calibration curve is generated. The resultant y=mx+b equation is used to generate the concentration of Ia in each sample.

Before each run, the capillary is flushed with running buffer (0.2 M phosphate, pH 6.8) for three minutes. After each 25 minute run, the capillary is flushed with 1 N NaOH for 1 minute, filtered HPLC water for 1 minute, 0.5 M phosphoric acid for 3 minutes, and filter HPLC water for 1 minute. The area under each peak is integrated and the peak area is determined and a final concentration is calculated from the standard curve.

7.5. Evaluation of B.t. Products

The amount of Ia present in various commercially available B.t. products is determined by capillary electrophoresis described in Section 6.4, supra. BACTOSPEINE™, JAVELIN™, NOVODOR™, SPHERIMOS™, BACTIMOS™, FORAY™, FLORBAC™ and BIOBIT™ are obtained from Novo Nordisk A/S. XENTARI™ and DIPEL™ are obtained from Abbott Laboratories. AGREE™ is obtained from Ciba-Geigy; MVP™ is obtained from Mycogen and CUTLASS™ is obtained from Ecogen.

The results are shown in Table III, infra and indicate that Ia is present in varying quantities ranging from less than 0.001 g Ia/BIU to 0.071 g Ia/BIU.

cellulose, salts, and vitamins are prepared in a 20 L heated kettle. This provides enough diet to test 10 to 12 samples with seven different concentrations of each test substance. The B.t. solutions are serially diluted to give 16 ml aliquots. Each aliquot is added to 184 g of molten diet. The mixture is subsequently homogenized and then poured into a plastic tray bearing 40 individual cells. Three control trays are prepared for each batch of diet. Once the diet has cooled and solidified, one insect of a known age (2–3 instar) is added to each cell, and the trays are covered with a perforated sheet of clear mylar. The trays are placed on racks and incubated for four days at 28° C. and 65% relative humidity.

After four days, insect mortality is rated. Each tray is given a sharp blow against a table top, and larvae that did not

TABLE III

Ia IN *Bacillus thuringiensis* PRODUCTS

| PRODUCT | type | Lot Number | Potency | Ia g/BIU |
|---|---|---|---|---|
| JAVELIN ™ WG | Btk | 9942281 | 32000 IU/mg | .071 |
| XENTARI ™ | Bta | 58715PG | 15000 IU/mg | .06 |
| AGREE ™ | Bta/Btk | RA208004 | 25000 IU/mg | .033 |
| BIOBIT ™ HPWP | Btk | 5012 | 48950 U/mg PIA | .018 |
| BIOBIT ™ FC | Btk | AG46669071 | 8 BIU/L | .013 |
| FORAY ™ 48B | Btk | BBN7018 | 12.6 BIU/L | .012 |
| DIPEL ™ | Btk | 58739PG | 32,000 IU/mg | .011 |
| FORAY ™ 76B | Btk | | 20.0 BIU/L | .007 |
| BACTOSPEINE ™ | Btk | B0B001 | 123653 IU/mg | .003 |
| BACTOSPEINE ™ | Btk | KX02A | 100,000 IU/mg | .003 |
| BACTOSPEINE ™ | Btk | WP | 16,000 IU/mg | <.001 |
| NOVODOR ™ | Btt | 9024 | 16.3 Million LTU/qt | $9.5 \times 10^{-9}$ g/LTU |
| FLORBAC ™ | Bta | 082-31-1 | 30,000 U/mg E | <.001 |
| SPHERIMOS ™ | B. sphr | BSN006 | | none |
| MVP ™ | Btk | 21193542 | | none |
| CUTLASS ™ | Btk/Btk | | | none |
| BACTIMOS ™ | Bti | BIB0024 | 11,700 IU/mg | none |

7.6. Diet Incorporation Bioassays

B.t.k. activity is determined by an artificial diet incorporation bioassay using third instar *Spodoptera exigua* larvae, second instar *Helicoverpa zea* larvae, third instar *Spodoptera frugiperda* larvae, second instar *Heliothis virescens* larvae, third instar *Trichoplusia ni* larvae, third instar *Pseudoplusia includens* larvae, third instar *Plutella xylostella* larvae, third instar *Spodoptera littoralis,* and third instar *Mamestra brassicae* larvae.

To determine the level of potentiation by adding Ia to B.t. products, and establish the range of insects that are affected, diet incorporation bioassays are performed. In the experiments with high concentrations of Ia against *Spodoptera exigua* (7.4–23.7 g Ia/BIU), purified Ia (70% active ingredient, 30% acetate counter ion) is used to potentiate BIOBIT™ FC (FC represents flowable concentrate). The remaining data presented in Table IV shows the potentiation of BIOBIT™ HPWP (high potency wettable powder) with Ia (0.658% active ingredient). *S. littoralis* and *M. brassicae* are tested using FLORBAC™ HPWP and Ia.

The various B.t. products are weighed and Ia is added to give 0.1 to 237 g Ia/BIU. The volume is adjusted with 0.1% Tween™. The samples are sonicated for 1 minute and then diluted to final volume. Neat samples (without Ia) and reference substances are prepared as well. Reference substances include B.t.k. HD-1-S-1980 (obtained from the NRRL) which is assigned a potency of 16,000 international units (IU) per milligram and JAVELIN™ WG which has been assigned a potency of 53,000 Spodoptera Units/mg (SU).

Standard artificial diet composed of water, agar, sugar, casein, wheat germ, methyl paraben, sorbic acid, linseed oil, move are counted as dead. Percent mortality is calculated and the data is analyzed via parallel probit analysis. $LC_{50}$s, $LC_{90}$s, the slope of the regression lines, coefficient of variation, and potencies are estimated. Samples are run a minimum of 3 times or until three potencies are within 20% of a calculated mean for each sample. To calculate the increase in activity associated with each concentration of Ia, the $LC_{50}$ of the B.t./Ia sample is corrected to reflect the amount of B.t. in the sample. The $Lc_{50}$s of the paired neat samples are divided by the corrected $LC_{50}$ values to give the fold reduction in $LC_{50}$ associated with Ia.

The following procedure is used to assay for *Lobesia bothrana*. Vine grapes attacked by *Lobesia bothrana* are collected in an unsprayed field and larva is removed. A dilution series of Ia (250 µg/ml, 500 µg/ml, and 1000 µg/ml) is made in water. One larva is put in the middle of the petri dish. If the larva is observed to drink, it is moved into a petri dish with freshly cut grape berries. The larvae are stored at 22° C. for 3–4 days.

As shown in Table IV, significant reductions in $LC_{50}$s are observed for all species.

TABLE IV

Diet Incorporation Bioassays

| Insect | g Ia per BIU | Increase in activity Fold reduction in $LC_{50}$ |
|---|---|---|
| *Spodoptera exigua* | 0.1 | 1.5 |
| (BIOBIT ™ HPWP) | 0.2 | 1.7 |

TABLE IV-continued

Diet Incorporation Bioassays

| Insect | g Ia per BIU | Increase in activity Fold reduction in $LC_{50}$ |
|---|---|---|
|  | 2.0 | 4.3 |
|  | 4.0 | 7.5 |
| Spodoptera exigua | 7.4 | 13 |
| (BIOBIT ™ FC) | 15 | 26 |
|  | 30 | 34 |
|  | 118 | 59 |
|  | 237 | 79 |
| Spodoptera frugiperda | 0.2 | 2.2 |
| (BIOBIT ™ HPWP) | 0.8 | 3.9 |
|  | 2.0 | 7.2 |
|  | 4.0 | 11.6 |
| Trichoplusia ni | 0.1 | 1.1 |
| (BIOBIT ™ HPWP) | 0.2 | 1.2 |
|  | 2.0 | 2.0 |
|  | 4.0 | 3.1 |
| Pseudoplusia includens | 0.1 | 0 |
| (BIOBIT ™ HPWP) | 0.2 | 1.2 |
|  | 0.8 | 2.1 |
|  | 2.0 | 2.4 |
|  | 4.0 | 3.4 |
| Plutella xylostella | 0.2 | 1.6 |
| (BIOBIT ™ HPWP) | 0.8 | 1.3 |
|  | 2.0 | 1.4 |
|  | 4.0 | 1.9 |
| Helicoverpa zea | 3.2 | 12.6 |
| (BIOBIT ™ HPWP) |  |  |
| Heliothis virescens | 3.2 | 4.2 |
| (BIOBIT ™ HPWP) |  |  |
| Lobesia bothrana | 2.0 | 3.0 |
| (BIOBIT ™ HPWP) |  |  |
| Spodoptera littoralis | 2.0 | 8.6 |
| (FLORBAC ™ HPWP) |  |  |
| Mamestra brassicae | 2.0 | 4.9 |
| (FLORBAC ™ HPWP) |  |  |

The potentiation of various produces on *Spodoptera exigua* by Ia is determined using diet incorporation bioassays described supra. Amounts of Ia added/BIU product are shown in Table V, infra. Ia/B.t. product mixture is incorporated into an agar-based wheat germ casein diet. The insects are placed on the diet for four days and held at 28° C. Mortality is recorded and analyzed using probit analysis. $LC_{50}$, $LC_{90}$ and potency are calculated from matched product lacking Ia. The results shown in Table V indicate that Ia potentiate various B.t.k. and B.t.a. products obtained from various sources. The B.t. strains contained in these products are described in Section 5.2., supra.

TABLE V

Potentiation of *B.t.* Products on *Spodoptera exigua*

| Product | g Ia per BIU | Increase in activity Fold reduction in $LC_{50}$ |
|---|---|---|
| BACTOSPEINE ™ WP | 0.4 | 1.04 |
|  | 1.7 | 2.3 |
| CONDOR ™ | 0.4 | 2.4 |
|  | 1.7 | 5.1 |
| AGREE ™ | 0.4 | 1.1 |
|  | 1.7 | 1.6 |
| CUTLASS ™ | 0.4 | 1.1 |
|  | 1.7 | 2.5 |
| MVP ™ | 0.4 | 6.0 |
|  | 1.7 | 7.7 |
|  | 2.0 | 12.1 |
| FLORBAC ™ HPWP | 0.2 | 1.1 |
|  | 0.8 | 2.0 |
| DIPEL ™ 2X | 0.2 | 1.2 |
|  | 0.8 | 2.3 |
|  | 2.0 | 3.9 |
| JAVELIN ™ WG | 0.2 | 0 |
|  | 0.8 | 1.08 |
|  | 2.0 | 2.9 |
| XENTARI ™ | 0.2 | 1.2 |
|  | 0.8 | 1.6 |
|  | 2.0 | 2.4 |

7.7. Foliar Bioassays

Foliar bioassays are performed with second instar *Spodoptera exigua* larvae on broccoli plants using BIOBIT™ FC and Ia. The ratio of Ia to BIOBIT™ FC is the same 2 g Ia/BIU BIOBIT™ FC. The treatments are applied to broccoli plants via a track sprayer in a carrier volume of 20 gallons per acre. Leaves are excised from the plants after the spray deposit had dried, and infested with second instar *Spodoptera exigua* larvae. The results are shown in Table VI, infra. 100% mortality is observed at a rate of 8.7 BIU/hectare BIOBIT™ FC+Ia, while BIOBIT™ FC alone killed 92% of the larvae at 58.8 BIU/hectare and 8% at 17.6 BIU/hectare. Treated plants are also placed in direct sunlight for eight hours, after which leaves are excised and infested. After eight hours in sunlight, BIOBIT™ FC alone at 58.8 BIU/hectare gave 27% mortality, while BIOBIT™ FC+Ia gave 100% mortality at 8.7 BIU/hectare.

A foliar assay done with early fourth instar larvae had BIOBIT™ FC alone with 75% mortality at 52 BIU/hectare, and BIOBIT™ FC (FC is flowable concentrate)+Ia gave 100% mortality at 13 BIU/hectare.

TABLE VI

Foliar Bioassays

| Treatment | BIU/hectare | % mortality | larval instar |
|---|---|---|---|
| BIOBIT ™ FC | 58.8 | 92% | 2 |
| BIOBIT ™ FC | 17.6 | 8% | 2 |
| BIOBIT ™ FC + Ia | 8.7 | 100% | 2 |
| BIOBIT ™ FC + 8 hr sunlight | 58.8 | 27% | 2 |
| BIOBIT ™ FC + Ia + 8 hr sunlight | 8.7 | 100% | 2 |
| BIOBIT ™ FC | 52 | 75% | 4 |
| BIOBIT ™ FC + Ia | 13 | 100% | 4 |

7.8. Field Trials

Field trials on garbonzo beans (*Spodoptera exigua*) demonstrated that BIOBIT™ FC alone at 70 BIU/hectare gave 51% control while 2 g Ia/BIU BIOBIT™ FC at 40 BIU/hectare provided 89% control (relative to no treatment). JAVELIN™ WG at 45 BIU/hectare gave 51% control.

Field trials on sweet corn (*Spodoptera frugiperda*) demonstrated that at 39.5 BIU/hectare, 2 g Ia/BIU BIOBIT™ FC provided 84% control.

7.9. Resistance Ratios

Colonies of susceptible and resistant *Plutella xylostella* are bioassayed. Resistant moths are field collected samples from Florida that have developed B.t. resistance following intensive exposure to JAVELIN™ WG. BIOBIT™ HPWP with Ia is analyzed using a leaf-dip bioassay. Resistance to JAVELIN™ and XENTARI™ is assayed without Ia. Six cm diameter cabbage leaf disks are dipped for 10 seconds into one of eight different concentrations of B.t. products or B.t./Ia formulations. Concentrations range from 1 to 1000 ppm. The leaf disks are allowed to air dry for two hours and placed in plastic petri dishes with second instar (0.2 to 0.4 mg) larvae. Twenty five insects/dose/day are replicated twice to give 50 insects/dose. After 72 hours at 27° C., mortality is recorded. Dose mortality regression is analyzed with probit analysis. Resistance ratios are calculated by dividing the $LC_{50}$ and $LC_{90}$ values of the susceptible moths. The results are shown in Table VII and indicate that the BIOBIT™ HPWP potentiates with 2 g Ia/BIU and 4 g Ia/BIU. Specifically, with 4 g Ia/BIU there is a 2 fold decrease in the $LC_{50}$ resistance ratio and a 10 fold decrease in the $LC_{90}$ resistance ratio.

TABLE VII

*Plutella xylostella* (B.t.k. Resistant) Resistance Ratios

| PRODUCT TESTED | $LC_{50}$ RR | $LC_{90}$ RR |
|---|---|---|
| JAVELIN ™ WG | 302.6 | 3829.7 |
| BIOBIT ™ HPWP | 20.5 | 98.5 |
| 2.0 g Ia/BIU BIOBIT ™ HPWP | 23.2 | 88.0 |
| 4.0 g Ia/BIU BIOBIT ™ HPWP | 10.4 | 11.5 |
| XENTARI ™ | 9.7 | 8.2 |

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

8. DEPOSIT OF MICROORGANISMS

The following strains of *Bacillus thuringiensis* have been deposited according to the Budapest Treaty in the Agricultural Research Service Patent Culture Collection (NRRL), Northern Regional Research Center, 1815 University Street, Peoria, Ill., 61604, USA.

| Strain | Accession Number | Deposit Date |
|---|---|---|
| EMCC0086 | NRRL B-21147 | October 6, 1993 |
| EMCC0087 | NRRL B-21148 | October 6, 1993 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

What is claimed is:

1. A method of obtaining a factor from a strain of *Bacillus thuringiensis* subsp. *kurstaki* or *Bacillus thuringiensis* subsp. *aizawai* comprising the steps of:
   (a) culturing said strain of *Bacillus thuringiensis* subsp. *kurstaki* or *Bacillus thuringiensis* subsp. *aizawai* to produce a fermentation broth having a supernatant;
   (b) collecting said supernatant; and then,
   (c) isolating a factor having $^1$H NMR shifts at about δ 1.5, 3.22, 3.29, 3.35, 3.43, 3.58, 3.73, 3.98, 4.07, 4.15, 4.25 and 4.35 and $^{13}$C shifts at about 31.6, 37.2, 51.1, 53.3, 54.0, 54.4, 61.5, 61.6, 64.1, 65.6, 158.3, 170.7 and 171.3 from said supernatant.

2. The method according to claim 1, wherein said factor is isolated from said supernatant by column chromatography.

3. The method of claim 1 in which said factor has the structure Ia

Ia

[Chemical structure: $H_2N$—C(=O)—NH—CH(C(O)NH$_2$)—CH$_2$—NH—C(=O)—CH(OH)—CH(NH$_2$)—CH(OH)—CH(OH)—CH(OH)—CH(NH$_2$)—CH$_2$—OH]

or salt thereof.

4. A method of obtaining a factor from strain *Bacillus thuringiensis* EMCC0086 having accession number NRRL B-21147 comprising the steps of:
   (a) culturing said strain to produce a fermentation broth having a supernatant;

(b) collecting said supernatant; and then, (c) isolating a factor having $^1$H NMR shifts at about δ 1.5, 3.22, 3.29, 3.35, 3.43, 3.58, 3.73, 3.98, 4.07, 4.15, 4.25 and 4.35 and $^{13}$C shifts at about 31.6, 37.2, 51.1, 53.3, 54.0, 54.4, 61.5, 61.6, 64.1, 65.6, 158.3, 170.7 and 171.3 from said supernatant.

5. The method according to claim 4 wherein said factor is isolated from said supernatant by column chromatography.

6. The method of claim 4 in which said factor has the structure Ia or salt thereof.

7. A method of obtaining a factor from strain *Bacillus thuringiensis* EMCC0087 having accession number NRRL B-21